(12) United States Patent
Kwok

(10) Patent No.: US 11,318,273 B2
(45) Date of Patent: May 3, 2022

(54) METHOD AND APPARATUS FOR HUMIDIFICATION OF BREATHABLE GAS WITH PROFILED DELIVERY

(71) Applicant: ResMed Pty Ltd, Bella Vista (AU)

(72) Inventor: Philip Rodney Kwok, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 0 days.

(21) Appl. No.: 17/207,577

(22) Filed: Mar. 19, 2021

(65) Prior Publication Data

US 2021/0205569 A1    Jul. 8, 2021

Related U.S. Application Data

(63) Continuation of application No. 16/251,054, filed on Jan. 17, 2019, now Pat. No. 11,077,282, which is a continuation of application No. 14/453,763, filed on Aug. 7, 2014, now Pat. No. 10,220,178, which is a continuation of application No. 13/194,050, filed on Jul. 29, 2011, now Pat. No. 8,833,367, which is a continuation of application No. 11/658,336, filed as application No. PCT/AU2005/001156 on Aug. 3, 2005, now Pat. No. 8,015,971.

(Continued)

(51) Int. Cl.
| | |
|---|---|
| *A61M 16/16* | (2006.01) |
| *A61M 16/00* | (2006.01) |
| *A61M 16/10* | (2006.01) |
| *A61M 16/20* | (2006.01) |

(52) U.S. Cl.
CPC ...... *A61M 16/161* (2014.02); *A61M 16/0003* (2014.02); *A61M 16/0051* (2013.01); *A61M 16/0066* (2013.01); *A61M 16/024* (2017.08); *A61M 16/109* (2014.02); *A61M 16/16* (2013.01); *A61M 16/20* (2013.01)

(58) Field of Classification Search
CPC ............ A61M 16/161; A61M 16/0003; A61M 16/109; A61M 16/024; A61M 16/0051; A61M 16/0066; A61M 16/16; A61M 16/20
See application file for complete search history.

(56) References Cited

U.S. PATENT DOCUMENTS

| | | | |
|---|---|---|---|
| 1,827,530 | A | 10/1931 | Le Grand |
| 4,014,382 | A | 3/1977 | Heath |

(Continued)

FOREIGN PATENT DOCUMENTS

| | | |
|---|---|---|
| DE | 10318383 | 7/2004 |
| EP | 535952 | 4/1993 |

(Continued)

OTHER PUBLICATIONS

Communication dated Oct. 30, 2018 issued in European Application No. 05769906.8 (7 pages).

(Continued)

*Primary Examiner* — Timothy A Stanis
(74) *Attorney, Agent, or Firm* — Fish & Richardson P.C.

(57) ABSTRACT

A method and apparatus for delivering breathable gas to a user includes a humidifying unit that is controllable to humidify the gas in accordance with a variable humidity profile such that the gas is delivered to the user at variable humidity levels, e.g., during a treatment session.

20 Claims, 2 Drawing Sheets

Related U.S. Application Data

(60) Provisional application No. 60/599,864, filed on Aug. 10, 2004.

(56) References Cited

U.S. PATENT DOCUMENTS

| | | | |
|---|---|---|---|
| 4,350,286 A | 9/1982 | Sutoh et al. | |
| 4,676,237 A | 6/1987 | Wood et al. | |
| 4,826,327 A | 5/1989 | Michell | |
| 4,921,642 A | 5/1990 | LaTorraca | |
| 5,062,145 A * | 10/1991 | Zwaan | A61M 16/16 392/396 |
| 5,148,710 A | 9/1992 | Gudehus et al. | |
| 5,165,398 A | 11/1992 | Bird | |
| 5,503,146 A | 4/1996 | Froehlich et al. | |
| 5,558,084 A | 9/1996 | Daniell et al. | |
| 5,769,071 A | 6/1998 | Turnbull | |
| 5,890,490 A | 4/1999 | Aylsworth et al. | |
| 6,050,260 A | 4/2000 | Daniell et al. | |
| 6,152,129 A | 11/2000 | Berthon-Jones | |
| 6,165,131 A | 12/2000 | Cnee et al. | |
| 6,240,921 B1 | 6/2001 | Brydon et al. | |
| 6,272,933 B1 | 8/2001 | Gradon et al. | |
| 6,349,724 B1 * | 2/2002 | Burton | F04D 25/166 128/204.18 |
| 6,397,841 B1 * | 6/2002 | Kenyon | A61M 16/0858 128/202.27 |
| 6,554,260 B1 | 4/2003 | Lipscombe et al. | |
| 6,584,972 B2 | 7/2003 | McPhee | |
| 6,588,412 B2 * | 7/2003 | Ferrara | F41B 11/52 124/49 |
| 6,626,175 B2 | 9/2003 | Jafari et al. | |
| 6,644,310 B1 | 11/2003 | Delache et al. | |
| 6,668,829 B2 | 12/2003 | Biondi et al. | |
| 7,137,388 B2 | 11/2006 | Virr et al. | |
| 7,306,205 B2 | 12/2007 | Huddart et al. | |
| 7,478,635 B2 | 1/2009 | Wixey et al. | |
| 7,516,740 B2 * | 4/2009 | Meier | A61M 16/16 128/203.16 |
| 2001/0050080 A1 * | 12/2001 | Seakins | A61M 16/024 128/203.16 |
| 2004/0016430 A1 | 1/2004 | Makinson et al. | |
| 2004/0055597 A1 | 3/2004 | Virr et al. | |
| 2004/0074493 A1 | 4/2004 | Seakins et al. | |
| 2004/0221844 A1 | 11/2004 | Hunt et al. | |
| 2004/0225179 A1 | 11/2004 | Kaplan et al. | |
| 2005/0116023 A1 | 6/2005 | Amundson et al. | |
| 2005/0217672 A1 * | 10/2005 | Bengtsson | A61M 16/204 128/204.18 |
| 2011/0297150 A1 | 12/2011 | Kwok | |
| 2014/0345614 A1 | 11/2014 | Kwok | |

FOREIGN PATENT DOCUMENTS

| | | |
|---|---|---|
| EP | 762107 | 3/1997 |
| EP | 0845277 | 6/1998 |
| EP | 0885623 | 12/1998 |
| EP | 1329240 | 7/2003 |
| GB | 2338420 | 12/1999 |
| JP | S57-101952 | 6/1982 |
| JP | H05-71790 | 3/1993 |
| JP | H05-317428 | 12/1993 |
| JP | H09-234347 | 9/1997 |
| JP | H10-179746 | 7/1998 |
| JP | H11-57009 | 3/1999 |
| JP | 2000-24109 | 1/2000 |
| JP | 2001-000553 | 1/2001 |
| JP | 4975621 | 7/2012 |
| WO | WO 01/013981 | 3/2001 |
| WO | WO 01/91841 | 12/2001 |
| WO | WO 02/066106 | 8/2002 |
| WO | WO 02/066107 | 8/2002 |
| WO | WO 03/018096 | 3/2003 |
| WO | WO 2004/020031 | 3/2004 |
| WO | WO 2004/039444 | 5/2004 |
| WO | WO 2006/015416 | 2/2006 |

OTHER PUBLICATIONS

Examination Report dated Nov. 25, 2011 in New Zealand Appln. No. 586728 (2 pages).
Examiner's First Report dated May 18, 2010 in Australian Appln. No. 2005270724 (2 pages).
International Search Report for PCT/AU2005/001156 dated Sep. 7, 2005 (4 pages).
Notice of Reasons for Rejection dated Jun. 9, 2014 issued in corresponding Japanese Application No. 2011-192458 (8 pages).
Notice of Reasons for Rejection dated Jan. 4, 2013 in Japanese Application No. 2011-192458, with English translation (8 pages).
Notice of Reasons for Rejection dated Jun. 28, 2011 in Japanese Appln. No. 2007-525125, with English translation(8 pages).
Notice of Reasons for Rejection dated Nov. 30, 2010 in Japanese Appln. No. 2007-525125, with English translation (6 pages).
Notice of Reasons for Rejection dated Sep. 24, 2013 in Japanese Application No. 2011-192458, with English translation (9 pages).
Notification of the First Office Action dated Sep. 3, 2014 issued in Chinese Application No. 201210353243.4 with English translation (16 pages).
Notification of the Fourth Office Action dated Mar. 23, 2016 issued in Chinese Application No. 201210353243.4 with English translation (11 pages).
Notification of the Second Office Action dated Apr. 23, 2015 issued in Chinese Application No. 201210353243.4 with English translation (16 pages).
Notification of the Second Office Action dated Dec. 8, 2011 in Chinese Appln. No. 200580026851.2, with English translation (10 pages).
Notification of the Third Office Action dated Sep. 30, 2015 issued in Chinese Application No. 201210353243.4 with English translation (9 pages).
Patent Examination Report No. 1 dated May 14, 2013 in Australian Application No. 2012200644 (3 pages).
PCT International Preliminary Report on Patentability in International Appln. No. PCT/AU2005/001156, dated Feb. 13, 2007, 5 pages.
Search Report dated May 17, 2017 issued in European Application No. 05769906.8 (10 pages).

* cited by examiner

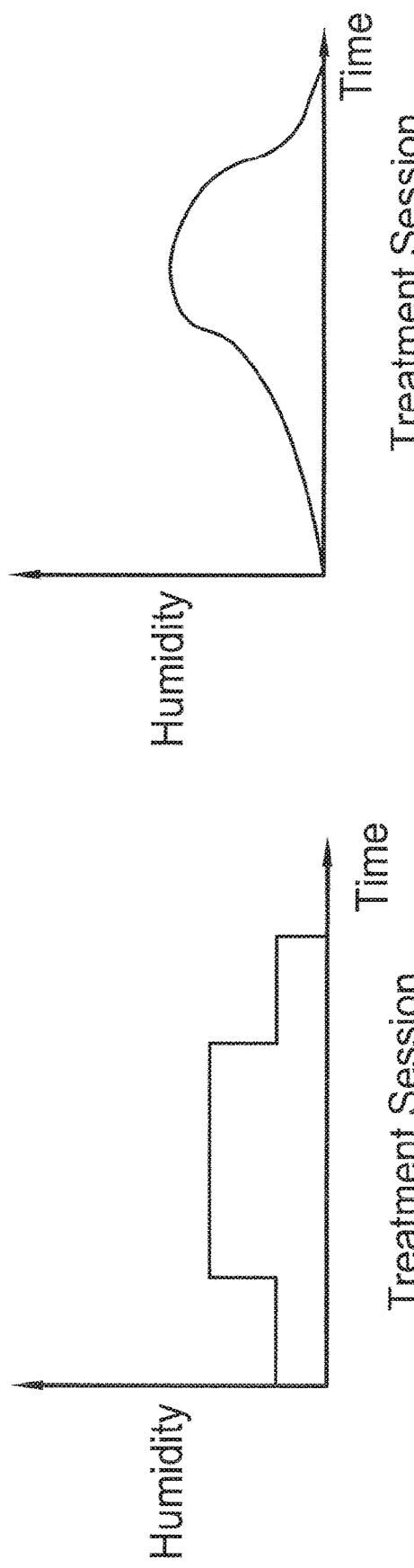
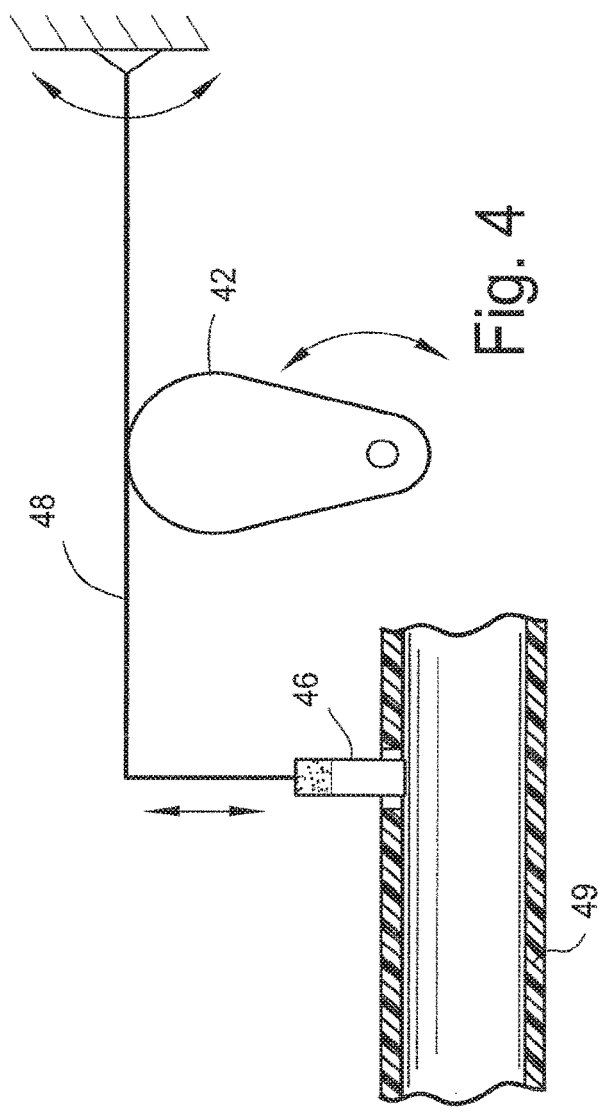

METHOD AND APPARATUS FOR HUMIDIFICATION OF BREATHABLE GAS WITH PROFILED DELIVERY

CROSS-REFERENCE TO RELATED APPLICATIONS

This application is a continuation of U.S. application Ser. No. 16/251,054, filed Jan. 17, 2019, which is a continuation of U.S. application Ser. No. 14/453,763, filed Aug. 7, 2014, now allowed, which is a continuation of U.S. application Ser. No. 13/194,050, filed Jul. 29, 2011 (issued as U.S. Pat. No. 8,833,367), which is a continuation of U.S. application Ser. No. 11/658,336, filed Jan. 24, 2007 (issued as U.S. Pat. No. 8,015,971), which is the U.S. national phase of international application PCT/AU2005/001156, filed Aug. 3, 2005, which designated the U.S. and claims the benefit of U.S. Provisional Application No. 60/599,864, filed Aug. 10, 2004, each of which is incorporated herein by reference in its entirety.

BACKGROUND OF THE INVENTION

Many humidifiers that are currently manufactured for patient respiratory disorders such as Obstructive Sleep Apnea (OSA) are large, bulky, and have large water reserves to treat most medical-related ailments such as dryness that may be caused by mouth leaks for example. Mouth leaks or any leaks for that matter release humidified gases to the atmosphere and bypasses the patient's airways where it is required. These heavy requirements including those medical conditions requiring high levels of continuous humidification may require humidifier devices with reserves as high as 600 mL of water. This increases the overall size and bulk of the Continuous Positive Airway Pressure (CPAP) Apparatus, ventilator, patient breathing air system, or gas supply system.

Where patients do not exhibit these inadvertent leaks or are only seeking lower levels of humidification, they are likely to be left with an unnecessarily oversized reservoir of remaining water at the end of a treatment session.

Furthermore, there are a substantial number of patients that only require relatively smaller amounts of humidification to marginally improve comfort to an acceptable level for a typical patient. These patients for example may include those that only use their conventional humidifiers (ResMed HUMIDAIRE™ or Fisher & Paykel HC100™) during the cooler months in winter for small but substantial gain in comfort by adding warmth and/or moisture to the airways that may dry due to the flow of air through the patient airways.

Current humidifiers are generally designed to fulfill the worst ailments and therefore require substantial humidification requirements. These systems could be regarded as 'overkill' for a substantial population of OSA patients who are only looking for a 'comfortable' level of improvement to undesirable dry and cool air.

Current and conventional humidification systems generally supply a continuous level of humidification as set by the user and dependent on the ambient temperature and humidity level. There are also systems that may modify humidification levels using a number of sensor arrays such as temperature sensors and/or humidity or flow sensors in aid to maximize efficiency and/or synchronize with pressure or airflow. These conventional systems can maximize the performance of the humidifier by being able to deliver the maximum amount of humidity whilst reducing or eliminating condensation (e.g. cooler air can carry less moisture), also known in the art as "rain-out". However, these types of sensor systems are complex and costly and still consume large amounts of water.

Accordingly, a need has developed in the art to address at least one of the shortcomings of the prior art humidifiers described above.

BRIEF SUMMARY OF THE INVENTION

One aspect of the invention to ameliorate the size and design constraints of the conventional humidifier whilst delivering an adequate and comfortable level of humidification whilst consuming/delivering the fluid (e.g. water, core gas vapor, etc.) in an efficient manner (requiring lower liquid reservoir volumes) and delivered according to the patient's needs, which may also be a manually selectable and/or programmable, semi-automated and/or automated delivery profile.

Another aspect of the invention relates to assisting patients looking for limited improvement to breathing comfort. However, the intention is not to replace conventional, continuously heated humidifiers, but rather to provide an additional choice more suitable for certain patients.

Another aspect of the invention provides profiled delivery of humidified gas to a patient.

Another aspect of the invention reduces water or fluid volume required by maximizing efficient use of water, which is a form of 'rationing'.

Another aspect of the invention aims to improve breathing comfort according to patient selectable profiles in one embodiment.

These and other aspects will be described in or apparent from the following detailed description.

BRIEF DESCRIPTION OF THE DRAWINGS

FIGS. 2 and 3 illustrate sample humidity profiles for a patient's treatment session; and FIG. 4 schematically illustrates an alternative embodiment of the present invention.

DETAILED DESCRIPTION OF PREFERRED EMBODIMENTS

Figure 1:
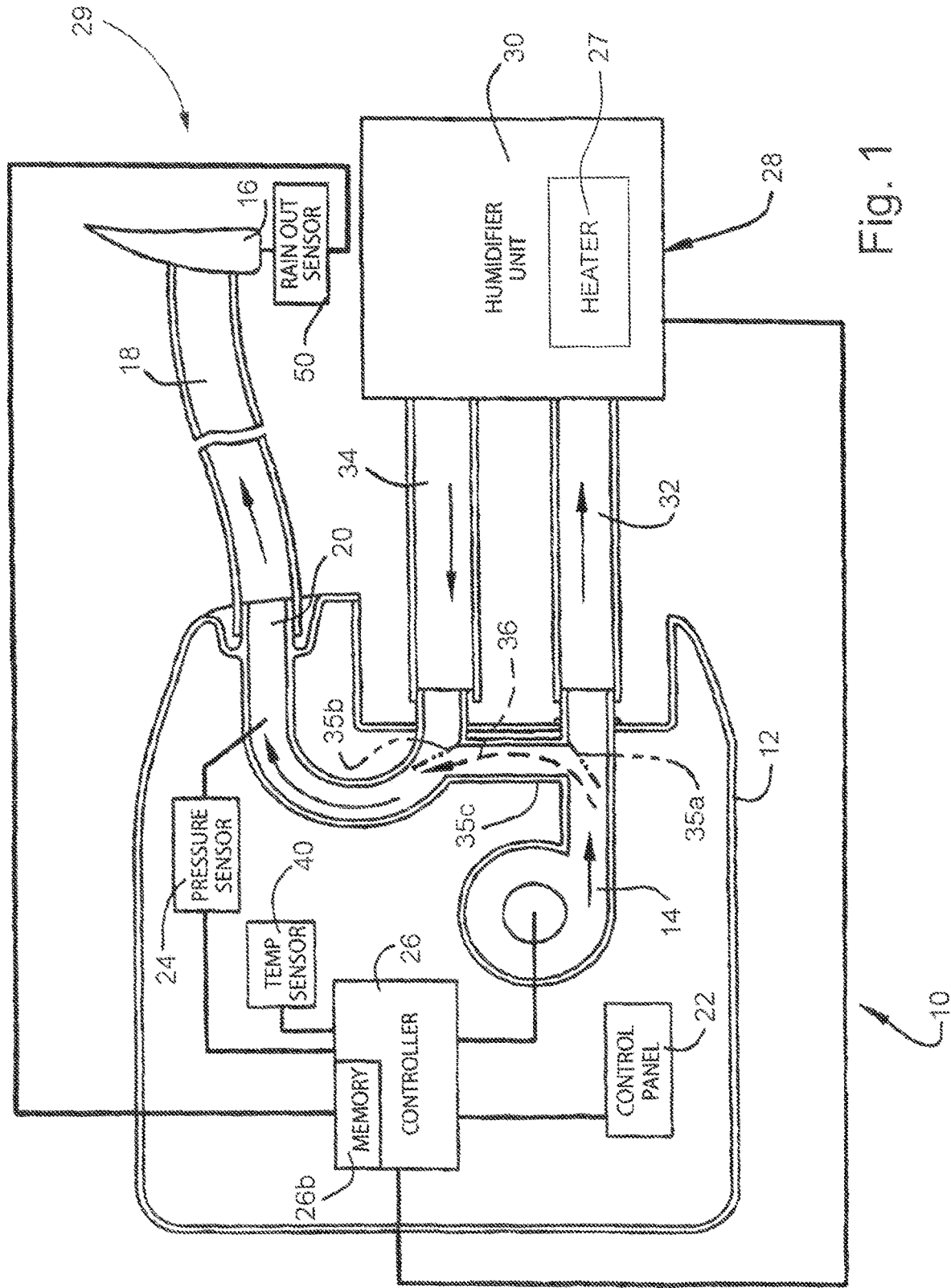
FIG. 1 is a schematic view of a blower according to an embodiment of the present invention.

FIG. 1 schematically illustrates a blower 10 according to an embodiment of the present invention. Blower 10 typically includes a housing 12 to support a blower motor 14 that pressurizes breathable gas for delivery to a patient interface 16 (e.g., a mask) via an air delivery conduit 18 that is connected to an outlet conduit 20 of blower 10. Blower 10 includes a control panel 22 with one or more buttons and preferably a display. Blower 10 includes a pressure sensor 24 to provide a signal to a controller 26 (e.g., CPU) for control of blower motor 14, in accordance with one or more control algorithms commercially available from ResMed, Inc.

Blower 10 is optionally provided with a selectively attachable and detachable humidifier unit 28 to form a humidifying system 29 that includes a tub 30 and one or more conduits 32, 34 that communicate with blower 10. Humidifier unit 28 may include structure as detailed in U.S. Published Patent Application No. 2004/0055597A1, incorporated by reference in its entirety. Humidifier unit 28 is in communication with controller 26, e.g., when conduits 32, 34 are attached to blower 10.

In one embodiment, the operation and/or performance of the humidifier unit 28 is tailored or profiled to suit the patient's specific humidification requirements. This in turn results in more efficient water usage, and allows the capacity of the tub 30 to be reduced. For example, the capacity of the tub 30 can be less than 400 mL, e.g., from 20 mL-400 mL or more preferably between 50 mL-200 mL. Of course, the volume capacity can be greater or less, depending on application. This reduced volume allows the overall size of the blower humidifier and/or assembly to be reduced, thereby removing design constraints and facilitating transport of the blower, e.g., during travel of the patient.

Profiling may be intermittent or profiled in accordance to a patient selectable profile or according to a selectable or semi/automated profile typical of the treatment session's ambient environment conditions.

Another embodiment may modify the delivery profile according to temperature of room over the course of a treatment session. The device may measure temperature versus time and predict what adjustments in profile are desirable to maintain efficient fluid/water use.

In another embodiment the profile may change over a set time period of treatment. For example, during an eight-hour treatment session, the profile begins at start of treatment and continues on to either end of session or a set time period on the device.

The above can obviously be used in combination with other embodiments such as watching average room temperature or even monitoring temperature changes over a period of hours, days, weeks, or months, and can modify the profile accordingly.

A profile may, for example, recognize that a typical bedroom tends to cool until the early hours of the morning where the temperature tends to stabilize before warming again by sunrise. Another profile that may be used may gradually reduce the humidity level during the course of the night in one simple form of the invention.

In embodiments, the invention may also postpone delivery until a period of the sleep session has passed. For example, a patient in the case of CPAP does not tend to go to sleep (beginning of treatment session) with dry airways. Their airways are probably going to dry later, say one hour into the night. Compared to conventional humidifiers used in OSA over eight-hour sessions, this feature alone can reduce humidification water volumes by one-eighth.

When implementing the delay feature, valves 35a and 35b can be used to divert the path of the air so as to by-pass the humidifier unit 28 via a by-pass conduit 35c. The air path is schematically illustrated in FIG. 1 with a broken arrow 36. When shut, valves 35a and 35b form part of the respective walls of gas conduits within blower 10.

The invention in one preferred embodiment may cycle between switch on and off during the course of the night. These cycles can be regular, irregular, or otherwise controlled for numerous intervals and various durations using some smart electronic control. The switching off does not necessarily need to completely switch off, but may reduce in temperature during periods where less humidification is required. As mentioned, this reduces water usage but may also lead to reduced energy (power) consumption and/or reduced running costs. For example, humidifier unit 28 may include a heater element 27 to heat the volume of water. The heater element 27 can be controlled via controller 26.

A user's manually selectable version is also possible. For example, as shown in FIGS. 2 and 3, a patient may set the humidifier device from a menu including, e.g., a Square wave or a Sinusoidal wave which may be integrated into blower 10 or humidifier unit 28 in the form of a symbol on a dial or push button. The device then humidifies the air to a level according to these changing profiles over a treatment session. In the case of a Sinusoidal wave setting where the cycle starts as a 'rise', the humidifier level increases gradually to a maximum during the middle of a treatment session and gradually reduces to the end of the treatment session. The profile can be symmetrical or asymmetrical. Also, the delay feature described above can be used in conjunction with the Square and/or Sinusoidal wave, so that humidity is added only after treatment has commenced.

If the humidifier provides instantaneous humidification on demand, this profile may also be adapted on a patient breath-by-breath basis rather than over a full treatment session.

These profiles mentioned above can be any combination or variation of a wave/curve and/or stepped. It may also be automated to learn the ambient environmental conditions. For example, a temperature sensor 40 (FIG. 1) may monitor room temperature changes over the annual seasons and modify the profile further to gain maximum water/fluid use and efficiency. For example, during cooler months, the humidification profile may allow for longer humidification periods (during the switch on or higher heat cycle) but not allow as high a level so as to reduce condensation and maximize comfort for the patient.

Another embodiment may include a 'fuzzy logic' version where the user, with the assistance of the device's intelligence, provides an optimum humidification profile, which provides optimal comfort to the patient whilst maintaining efficient fluid/water usage. In this example, the patient may wake up and press one of three buttons, or select a dial setting, to indicate whether the level of humidification was "okay", "too little" or "too much". The device can then re-profile the delivery according to the patient's perceived comfort level. In this case, much of the actual profiling is automated.

Another embodiment of the invention considers two positive aspects of humidification and provides additional benefits. Current technology warms the patient breathing air. Warm air is considered more comfortable to breathe especially if the ambient temperature is relatively low. Secondly, humidifiers add moisture to the breathing air. The invention may profile the humidity level at a different rate to that of the air temperature. For example, according to the Sinusoidal wave setting example mentioned earlier, the device may maintain warm breathing air with minimal increased requirement at the middle of the treatment session. The humidity however may increase at an independent level relative to the temperature; for example, the humidity may increase much more than the temperature at the peak of the wave profile. This can again be selected by a patient according to their comfort requirements.

Any of the embodiments mentioned above may have an ability to transfer any 'learned' logic by memory storage media, or wireless communication (e.g. "Blue tooth" technology) so that the logic could be utilized by a physician, another user, or else simply because the patient intends to replace the device or upgrade to a newer model. Controller 26 may include a memory 26b to facilitate data storage/transfer.

In a more mechanized embodiment of the invention, a simple valve that controls the humidified air entering the mainstream breathing air may be controlled by mechanical links. For example, as shown in FIG. 4, a rotating cam 42 that is profiled to control a valve 46 via mechanical linkage 48, thus producing staged delivery of humidified gas through a conduit 49 (which may be conduit 34 in FIG. 1). The cam profile can be such that the peak of the cam's lobe translates to largest valve opening and therefore greatest humidification level. The cam 42 could be designed to turn one revolution in one treatment session. The shape of the cam lobe determines the delivery profile. A bi-metallic spring may also be added to modify lift (generally reduce lift to reduce humidification as temperature decreases) and therefore forms a type of mechanical temperature compensation.

Further to the above embodiment, the profile could be mechanically adjustable by a user. For example, a number of selectable pins around the perimeter of a cam lobe could be push in or out to modify at what period of the session and by how much to lift the valve.

In another embodiment, the invention may also incorporate a switch or sensor device that switches off the humidifier should the treatment session be interrupted. For example, an OSA patient may get up in the middle of the night to go to the bathroom. This feature is designed to reduce water consumption further and also prevent condensation in the air delivery pipe, especially if the flow generator has stopped (ResMed's Smart Stop™ feature). It may also prevent the patient breathing in condensate when they return to bed, which in turn improves patient comfort.

Yet another embodiment of the invention includes a mask "rain-out" sensor 50 (FIG. 1) that does not require the use of humidity sensor like the prior art. An infrared emitter and detector in communication with controller 26, e.g., are placed at the bottom of the mask interface or location where condensation is likely to bead or pool. The mask frame wall in front of the side-by-side emitter/detector is transparent to infrared light. Under normal conditions, the detector does not see any infrared light. If significant water droplets develop (condensation) in front of the emitter/detector, the light reflects back to the detector and signifies condensation. The device may also use another type of visible or non-visible light emitter/detector combination.

The above feature applied to the invention may either reduce humidification or heating in response to "rain-out", or otherwise it may modify the humidification delivery profiles as described earlier to improve patient comfort. Also by identifying "rain-out", this may provide intelligence to the device's control that the ambient temperature is falling or the heating of the delivered air is too low to carry the current level of moisture.

One or more of the following advantages may be realized in accordance with preferred embodiments of the invention:

Humidifier that is smaller, easier to store or travel with.

A device that can be tailored (profiled) or set by a user to suit their circumstances, needs or desires for comfort.

A profile humidifier may bridge the gap between inefficient "Passover" (non-heated) humidifiers and fully featured heated humidifiers that treat most dry airway ailments.

Potentially less complaints of "rain-out" or condensation as patients may have adjusted their device to a high setting, only to find that a cooling room creates increased condensation.

Ability to control, modify and fine-tune their patient's therapy.

By minimizing humidity delivery when it is not necessary reduces water usage and reservoir volume required, therefore reducing device size.

Alleviates the size constraints on engineers for the OSA market that is trending towards fewer design compromises to meet comfort expectations.

Flow generators have already been reduced in size, whereas the humidifier is about the same size as next generation flow generators, if not larger. This concept gives users the perception of even more compact dimension that is potentially lighter and easier to transport.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the invention. For example, the above described preferred embodiments of the invention may be adapted to any humidification device whether to treat OSA or used in any gas breathing system.

The invention claimed is:

1. A system configured to provide respiratory therapy, the system comprising:

a housing;

a blower adapted to generate a supply of pressurized breathable gas for respiratory therapy, the blower being positioned within the housing;

a tub adapted to hold a volume of water, the tub including (i) a tub inlet configured to receive the supply of pressurized breathable gas and (ii) a tub outlet configured to output a supply of pressurized breathable gas with added humidification;

a first outlet that is fluidly coupled to the blower, the first outlet being formed in and extending outwardly from a sidewall of the housing, wherein the first outlet is configured to be removably connected with the tub inlet to provide the supply of pressurized breathable gas to the tub;

an inlet formed in and extending from the sidewall of the housing, wherein the inlet is configured to be removably connected with the tub outlet to receive the supply of pressurized breathable gas with added humidification from the tub;

a second outlet that is in fluid communication with the inlet via an internal conduit within the housing, wherein the second outlet is formed in and extends outwardly from a different wall of the housing, the second outlet being configured to be removably connected with a first end of an air delivery conduit to provide the supply of pressurized breathable gas with added humidification to the air delivery conduit, wherein a second end of the air delivery conduit is in fluid communication with a patient interface and is configured to provide the supply of pressurized breathable gas with added humidification to a patient via the patient interface;

a heater element configured to heat the volume of water contained in the tub; and a controller contained within the housing that is communicatively coupled to the blower and the heater element, wherein the controller is configured to (i) while providing respiratory therapy, control the blower and the heater element to provide the supply of pressurized breathable gas with added humidification to the air delivery conduit by activating the blower and the heating element, and (ii) after stopping the respiratory therapy, control the blower and the heater element to provide the supply of the pressurized breathable gas without added humidification to the air delivery conduit by activating the blower and deactivating the heating element.

2. The system of claim 1, wherein:
the first outlet and the inlet are positioned adjacent to each other along and with a common orientation relative to the sidewall of the housing, and
the tub inlet and the tub outlet are positioned adjacent to each other and with a complementary orientation to the common orientation of the first outlet and inlet.

3. The system of claim 2, wherein:
the first outlet and the inlet are positioned a distance apart along the sidewall, and
the tub inlet and the tub are positioned a complementary distance apart so as to permit for simultaneous connection of (i) the first outlet and the tub inlet, and (ii) the inlet and the tub outlet.

4. The system of claim 3, wherein:
the internal conduit includes a curved portion that is configured to change the supply of pressurized breathable gas with added humidification from a first direction upon entering the inlet to a second direction upon exiting the second outlet, wherein the first direction is different from the second direction.

5. The system of claim 4, wherein the first direction differs from the second direction by at least 90 degrees.

6. The system of claim 3, wherein:
the first outlet and the inlet comprise male fittings, and
the tub inlet and the tub outlet comprise female fittings that are configured to be removably connected around the male fittings.

7. The system of claim 6, wherein:
the second outlet comprises a male fitting, and
the first end of the air delivery conduit comprises a female fitting that is configured to be removably connected around the second outlet.

8. The system of claim 1, further comprising:
a temperature sensor;
wherein the controller is further configured to control the blower and the heater element based, at least in part, on a temperature signal provided by the temperature sensor while providing the respiratory therapy.

9. The system of claim 1, further comprising:
a pressure sensor;
wherein the controller is further configured to control the blower and the heater element based, at least in part, on a pressure signal provided by the pressure sensor while providing the respiratory therapy.

10. The system of claim 9, further comprising:
a temperature sensor;
wherein the controller is further configured to control the blower and the heater element additionally based, at least in part, on a temperature signal provided by the temperature sensor while providing the respiratory therapy.

11. The system of claim 1, further comprising:
a profile;
wherein the controller is further configured to control the blower and the heater element based, at least in part, on the profile.

12. The system of claim 11, further comprising:
a control panel that provides a user interface, wherein the user interface is configured to receive user selection of the profile via the user interface;
wherein the controller is configured to, in response to receiving the user input, control the blower and the heater element based, at least in part on the profile.

13. The system of claim 12, wherein the profile comprises a profile to provide respiratory therapy that directs the controller to control the blower and the heater element to provide the supply of pressurized breathable gas with added humidification to the air delivery conduit by activating the blower and the heating element.

14. The system of claim 13, wherein the profile designates levels of operation for activating the blower and for activating the heating element over time to provide the respiratory therapy.

15. The system of claim 12, wherein the profile comprises a profile to reduce humidification in, at least, the air delivery conduit after stopping the respiratory therapy that directs the controller to control the blower and the heater element to provide the supply of the pressurized breathable gas without added humidification to the air delivery conduit by activating the blower and deactivating the heating element.

16. The system of claim 15, wherein the profile designates one or more levels of operation for activating the blower and an off state for the heating element.

17. The system of claim 16, wherein activating the heater element comprises turning the heater element on and deactivating the heater element comprises turning the heater element off.

18. The system of claim 1, wherein stopping the respiratory therapy comprises a respiratory therapy session being interrupted.

19. The system of claim 1, wherein stopping the respiratory therapy comprises an end of a respiratory therapy session.

20. The system of claim 1, wherein stopping the respiratory therapy comprises a time period having elapsed.

* * * * *